United States Patent
MacDonald et al.

(10) Patent No.: US 12,336,797 B2
(45) Date of Patent: Jun. 24, 2025

(54) WRIST-WORN ELECTRONIC DEVICE WITH OPTICAL CARDIAC MONITOR

(71) Applicant: Garmin International, Inc., Olathe, KS (US)

(72) Inventors: Paul R. MacDonald, Calgary (CA); Christopher J. Kulach, Cochrane (CA); Tim A. Verschaeve, Calgary (CA); Benjamin A. Primeau, Calgary (CA)

(73) Assignee: Garmin International, Inc., Olathe, KS (US)

( * ) Notice: Subject to any disclaimer, the term of this patent is extended or adjusted under 35 U.S.C. 154(b) by 151 days.

(21) Appl. No.: 18/460,256

(22) Filed: Sep. 1, 2023

(65) Prior Publication Data
US 2024/0138693 A1 May 2, 2024

Related U.S. Application Data

(60) Provisional application No. 63/419,606, filed on Oct. 26, 2022.

(51) Int. Cl.
*A61B 5/024* (2006.01)
*A61B 5/00* (2006.01)
*A61B 5/1455* (2006.01)

(52) U.S. Cl.
CPC ...... *A61B 5/02433* (2013.01); *A61B 5/02438* (2013.01); *A61B 5/14552* (2013.01); *A61B 5/681* (2013.01); *A61B 5/7221* (2013.01)

(58) Field of Classification Search
CPC ............ A61B 5/02416; A61B 5/02427; A61B 5/02433; A61B 5/14522; A61B 5/02438; A61B 5/681; A61B 5/6824; A61B 5/7221
See application file for complete search history.

(56) References Cited

U.S. PATENT DOCUMENTS

| | | |
|---|---|---|
| 4,258,719 A | 3/1981 | Lewyn |
| 5,277,181 A | 1/1994 | Mendelson et al. |

(Continued)

FOREIGN PATENT DOCUMENTS

| | | |
|---|---|---|
| EP | 0319160 A1 | 6/1989 |
| EP | 3111834 A1 | 1/2017 |

(Continued)

OTHER PUBLICATIONS

U.S. Appl. No. 15/860,865, filed Feb. 9, 2021, Macdonald et al.

(Continued)

*Primary Examiner* — Colin T. Sakamoto
(74) *Attorney, Agent, or Firm* — Samuel M. Korte; Max M. Ali

(57) ABSTRACT

A wrist-worn electronic device comprises a housing including a bottom wall configured to contact a user's wrist, an optical transmitter and receiver assembly and a processor. The optical transmitter and receiver assembly comprises a first optical transmitter array, a first optical receiver, a second optical transmitter array, and a second optical receiver. The first and second optical transmitter arrays transmit a plurality of first and second optical signals, respectively, that pass through a user's skin. The first and second optical receivers receive the first and second optical signals that travel along a first signal path and a second signal path, respectively, that are both substantially parallel to an arm axis of the user. The processor is configured determine physiological information about the user based on one or both of first and second electronic signals corresponding to the first and second optical signals.

20 Claims, 6 Drawing Sheets

(56) References Cited

U.S. PATENT DOCUMENTS

| | | |
|---|---|---|
| 5,431,170 A | 7/1995 | Mathews |
| 5,524,617 A | 6/1996 | Mannheimer |
| 5,632,272 A | 5/1997 | Diab et al. |
| 6,178,343 B1 | 1/2001 | Bindszus et al. |
| 6,702,752 B2 | 3/2004 | Dekker |
| 6,997,879 B1 | 2/2006 | Turcott |
| 7,035,679 B2 | 4/2006 | Addison et al. |
| 7,169,110 B2 | 1/2007 | Lee et al. |
| 7,215,987 B1 | 5/2007 | Sterling et al. |
| 7,336,982 B2 | 2/2008 | Yoo |
| 7,470,234 B1 | 12/2008 | Elhag et al. |
| 7,625,344 B1 | 12/2009 | Brady et al. |
| 7,729,748 B2 | 6/2010 | Florian |
| 7,794,406 B2 | 9/2010 | Reisfeld et al. |
| 7,867,142 B2 | 1/2011 | Kim et al. |
| 8,109,874 B2 | 2/2012 | Kong et al. |
| 8,251,903 B2 | 8/2012 | Leboeuf et al. |
| 8,260,405 B2 | 9/2012 | Aarts |
| 8,460,199 B2 | 6/2013 | Rulkov et al. |
| 8,463,347 B2 | 6/2013 | Watson et al. |
| 8,509,882 B2 | 8/2013 | Albert et al. |
| 8,512,242 B2 | 8/2013 | Leboeuf et al. |
| 8,554,297 B2 | 10/2013 | Moon et al. |
| 8,591,411 B2 | 11/2013 | Banet et al. |
| 8,647,270 B2 | 2/2014 | Leboeuf et al. |
| 8,652,040 B2 | 2/2014 | Leboeuf et al. |
| 8,670,123 B2 | 3/2014 | Schleipen et al. |
| 8,700,111 B2 | 4/2014 | Leboeuf et al. |
| 8,788,002 B2 | 7/2014 | Leboeuf et al. |
| 8,827,906 B2 | 9/2014 | Yuen et al. |
| 8,886,269 B2 | 11/2014 | Leboeuf et al. |
| 8,888,701 B2 | 11/2014 | Leboeuf et al. |
| 8,923,941 B2 | 12/2014 | Leboeuf et al. |
| 8,929,965 B2 | 1/2015 | Leboeuf et al. |
| 8,929,966 B2 | 1/2015 | Leboeuf et al. |
| 8,934,952 B2 | 1/2015 | Leboeuf et al. |
| 8,942,776 B2 | 1/2015 | Leboeuf et al. |
| 8,945,017 B2 | 2/2015 | Venkatraman et al. |
| 8,954,135 B2 | 2/2015 | Yuen et al. |
| 8,974,396 B1 | 3/2015 | Brady et al. |
| 8,989,830 B2 | 3/2015 | Leboeuf et al. |
| 8,998,815 B2 | 4/2015 | Venkatraman et al. |
| 9,005,129 B2 | 4/2015 | Venkatraman et al. |
| 9,014,790 B2 | 4/2015 | Richards et al. |
| 9,039,614 B2 | 5/2015 | Yuen et al. |
| 9,044,171 B2 | 6/2015 | Venkatraman et al. |
| 9,044,180 B2 | 6/2015 | Leboeuf et al. |
| 9,131,312 B2 | 9/2015 | Leboeuf et al. |
| 9,289,135 B2 | 3/2016 | Leboeuf et al. |
| 9,289,175 B2 | 3/2016 | Leboeuf et al. |
| 9,292,008 B1 | 3/2016 | Ahamed et al. |
| 9,301,696 B2 | 4/2016 | Leboeuf et al. |
| 9,307,917 B2 | 4/2016 | Hong et al. |
| 9,314,167 B2 | 4/2016 | Leboeuf et al. |
| 9,538,921 B2 | 1/2017 | Leboeuf et al. |
| 9,717,424 B2 | 8/2017 | Kulach |
| 9,801,587 B2 | 10/2017 | MacDonald et al. |
| 10,215,698 B2 | 2/2019 | Han et al. |
| 10,568,525 B1 | 2/2020 | Wu et al. |
| 10,905,382 B2 | 2/2021 | Lee et al. |
| 10,912,469 B2 | 2/2021 | MacDonald et al. |
| 11,179,051 B2 | 11/2021 | Kulach et al. |
| 2003/0109775 A1 | 6/2003 | O'Neil et al. |
| 2005/0143665 A1 | 6/2005 | Huiku et al. |
| 2009/0048526 A1 | 2/2009 | Aarts et al. |
| 2009/0105556 A1 | 4/2009 | Fricke et al. |
| 2009/0259116 A1 | 10/2009 | Wasserman et al. |
| 2010/0113948 A1 | 5/2010 | Yang et al. |
| 2011/0054277 A1 | 3/2011 | Pinter et al. |
| 2011/0060200 A1 | 3/2011 | Bernreuter |
| 2011/0082355 A1 | 4/2011 | Eisen et al. |
| 2012/0197137 A1 | 8/2012 | Jeanne et al. |
| 2012/0209095 A1 | 8/2012 | Huiku |
| 2013/0030267 A1 | 1/2013 | Lisogurski et al. |
| 2013/0231926 A1 | 9/2013 | Gigi |
| 2013/0261415 A1 | 10/2013 | Ashe et al. |
| 2014/0213858 A1 | 7/2014 | Presura et al. |
| 2014/0213863 A1 | 7/2014 | Loseu et al. |
| 2014/0276099 A1 | 9/2014 | Kirenko et al. |
| 2014/0288436 A1 | 9/2014 | Venkatraman et al. |
| 2014/0316305 A1 | 10/2014 | Venkatraman et al. |
| 2015/0065889 A1 | 3/2015 | Gandelman et al. |
| 2015/0173628 A1 | 6/2015 | Yuen et al. |
| 2015/0196256 A1 | 7/2015 | Venkatraman et al. |
| 2015/0208950 A1 | 7/2015 | Akl et al. |
| 2015/0230743 A1 | 8/2015 | Silveira et al. |
| 2015/0313549 A1 | 11/2015 | Lee et al. |
| 2016/0051158 A1 | 2/2016 | Silva |
| 2016/0235313 A1 | 8/2016 | Sharma et al. |
| 2016/0287107 A1 | 10/2016 | Szabados et al. |
| 2016/0296174 A1 | 10/2016 | Isikman et al. |
| 2016/0317096 A1 | 11/2016 | Adams et al. |
| 2016/0317097 A1 | 11/2016 | Adams et al. |
| 2017/0020399 A1 | 1/2017 | Shemesh et al. |
| 2017/0281027 A1 | 10/2017 | Altmejd et al. |
| 2018/0235483 A1 | 8/2018 | Mouradian |
| 2018/0317785 A1* | 11/2018 | MacDonald ....... A61B 5/02438 |
| 2018/0317786 A1 | 11/2018 | Kulach et al. |
| 2018/0317852 A1* | 11/2018 | MacDonald ....... A61B 5/14542 |
| 2018/0353134 A1 | 12/2018 | Walter et al. |
| 2020/0146569 A1* | 5/2020 | Lee ..................... A61B 5/7221 |
| 2020/0187943 A1 | 6/2020 | Shelton, IV et al. |
| 2020/0297226 A1* | 9/2020 | LeFrancois ........ A61B 5/02427 |
| 2021/0330209 A1* | 10/2021 | Nadeau ................ A61B 5/6824 |
| 2022/0022766 A1 | 1/2022 | Kulach et al. |
| 2022/0142569 A1 | 5/2022 | Tsai et al. |

FOREIGN PATENT DOCUMENTS

| | | |
|---|---|---|
| KR | 1020180045382 | 5/2018 |
| WO | 2006067690 A2 | 6/2006 |
| WO | 2011051888 A2 | 5/2011 |
| WO | 2013042070 A1 | 3/2013 |
| WO | 2013124750 A1 | 8/2013 |
| WO | 2013190423 A1 | 12/2013 |
| WO | 2015116891 A1 | 8/2015 |
| WO | 2017027551 A1 | 2/2017 |
| WO | 2017089921 A1 | 6/2017 |

OTHER PUBLICATIONS

Abstract of Lee et al., Publication Date: Dec. 5, 2018, 1 pp. (Year: 2018).

Casson et al., Gyroscope vs. accelerometer measurements of motion from wrist PPG, during physical exercise, School of Electrical and Electronic Engineering, The University of Manchester, Manchester, UK, ICT Express 2, 2016, p. 175-179.

International Search Report and Written opinion from PCT/EP2018/061445 dated Aug. 16, 2018.

International Search Report and Written Opinion from PCT/EP2018/061446 dated Aug. 16, 2018.

International Search Report and Written Opinion from PCT/EP2019/061444 dated Aug. 16, 2018.

Konijnenburg et al., A Battery-Powered Efficient Multi-Sensor Acquisition System with Simultaneous ECG, BIO-Z, GSR, and PPG, 2016 IEEE International Solid-State Circuits Conference, ISSCC 2016/ Session 28/ Biological Sensors for Point of Care/ 28.4, 3 pp. (Year: 2016).

Lee et al., Bidirectional Recurrent Auto-Encoder for Photoplethysmogram Denoising, Publication Date: Dec. 5, 2018, IEEE Journal of Biomedical and Health informatics, 2018, pp. (Year: 2018).

Nitzan et al., Pulse oximetry: fundamentals and technology update, Dove Press journal, Medical Devices: Evidence and Research Jul. 8, 2014.

Nogawa et al., Development of an optical arterial hematocrit measurement method: pulse hematometry. Engineering in Medicine and Biology 27th Annual Conference, Sep. 1-4, 2005.

Printout from https://www.apple.com/newsroom/2018/09/redesigned-apple-watch-series-4-revolutionizes-communication-fitness-and-health/ published prior to Mar. 16, 2020.

(56) References Cited

OTHER PUBLICATIONS

Printout from https://www.dcrainmaker.com/2022/01/garmin-fenix7-7s-7x-in-depth-review.html published prior to Sep. 1, 2023.
Printout from https://www.dcrainmaker.com/2022/04/garmin-vivosmart-5-in-depth-review.html published prior to Sep. 1, 2023.
Printout from https://www.dcrainmaker.com/2022/09/apple-watch-ultra-in-depth-review-its-a-start.html published prior to Sep. 1, 2023.
Printout from https://www.pcmag.com/reviews/apple-watch-series-4 published prior to Mar. 16, 2020.
Wieben, O., Light Absorbance in Pulse Oximetry, published prior to Jan. 3, 2018.
Yadhuraj et al., Motion Artifact Reduction in Photoplethysmographic Signals: A Review, International Journal of Innovative Research & Development, Mar. 2013, vol. 2, Issue 3, p. 626-640.
International Search Report and Written opinion from PCT/US2023/077415, dated Feb. 14, 2024.

\* cited by examiner

WRIST-WORN ELECTRONIC DEVICE WITH OPTICAL CARDIAC MONITOR

RELATED APPLICATIONS

This patent application is a non-provisional utility patent application which claims priority benefit, with regard to all common subject matter, under 35 U.S.C. § 119(e) of earlier-filed U.S. provisional application 63/419,606, filed Oct. 26, 2022, and entitled "IMPROVED OPTICAL CARDIAC MONITOR." The Provisional Application is hereby incorporated by reference in its entirety.

BACKGROUND

An electronic fitness device may provide optical cardiac monitoring of a user of the device. The user may wear the electronic device such that a housing of the electronic device is located in contact with the skin of the user— typically being worn on the user's wrist. The cardiac monitoring functionality may include physiological information such as a user's heart rate and pulse oximetry. The electronic fitness device may include optical devices, such as an optical transmitter, which emits an optical signal into the user's skin, and an optical receiver, which receives transmissions or reflections of the optical signal from the skin and generates a photoplethysmogram (PPG) signal corresponding to the intensity of the received optical signal. The electronic fitness device processes the PPG signal to determine the user's heart rate and pulse oximetry. Occasionally, while the user is active or exercising, the electronic fitness device may move out of a normal position and become tilted on the user's wrist. In this situation, the optical transmitter and/or the optical receiver may become separated from the user's skin—leading to a lower optical signal level and a reduction in a signal to noise ratio of the PPG signal. Under these circumstances, the electronic fitness device may not be able to accurately determine the user's heart rate and pulse oximetry.

BRIEF DESCRIPTION OF THE DRAWINGS

Embodiments of the current technology are described in detail below with reference to the attached drawing figures, which are referenced in the detailed description. The use of the same reference numbers in different instances in the description and the figures may indicate similar or identical items.

Figure 1A:
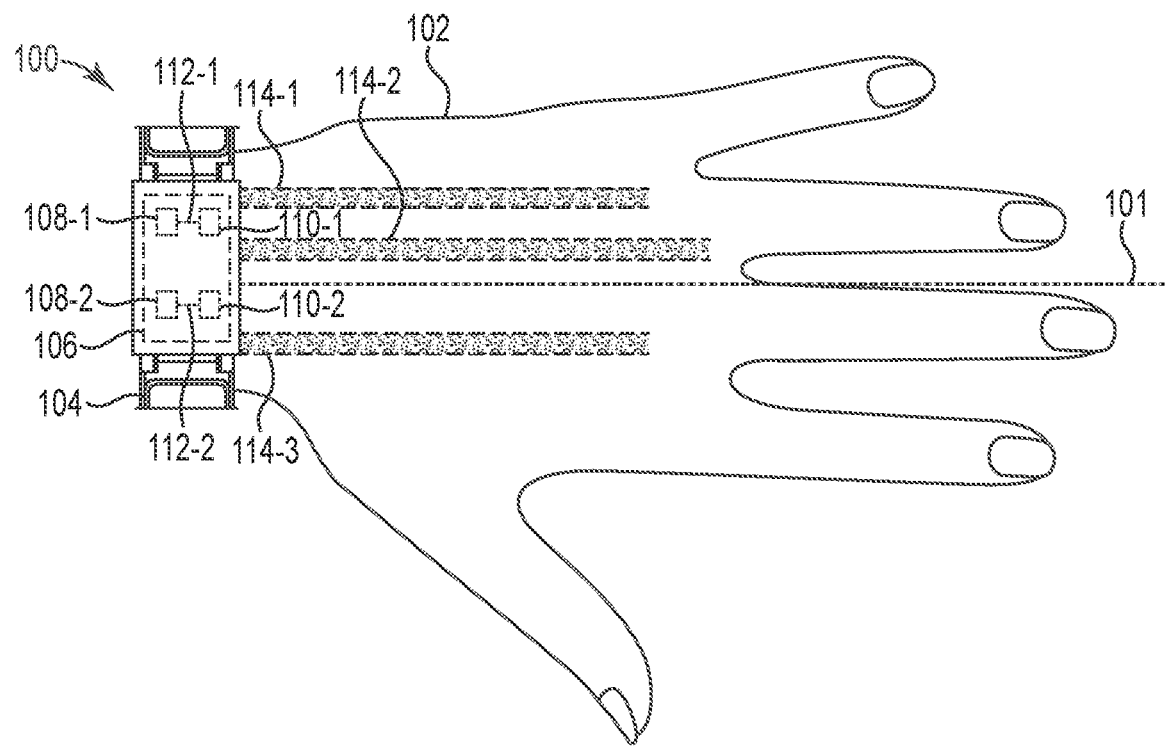
FIG. 1A illustrates a top view of a wrist-worn electronic device, constructed in accordance with various embodiments of the present technology, worn on a user's wrist.

The drawing figures do not limit the current invention to the specific embodiments disclosed and described herein. The drawings are not necessarily to scale, emphasis instead being placed upon clearly illustrating the principles of the invention.

DETAILED DESCRIPTION OF THE INVENTION

The following detailed description of the technology references the accompanying drawings that illustrate specific embodiments in which the technology can be practiced. The embodiments are intended to describe aspects of the technology in sufficient detail to enable those skilled in the art to practice the technology. Other embodiments can be utilized and changes can be made without departing from the scope of the current invention. The following detailed description is, therefore, not to be taken in a limiting sense. The scope of the current technology is defined only by the appended claims, along with the full scope of equivalents to which such claims are entitled.

Relational and/or directional terms, such as "above", "below", "up", "upper", "upward", "down", "downward", "lower", "top", "bottom", "outer", "inner", etc., along with orientation terms, such as "horizontal" and "vertical", may be used throughout this description. These terms retain their commonly accepted definitions and are used with reference to embodiments of the technology and the positions, directions, and orientations thereof shown in the accompanying figures. Embodiments of the technology may be positioned and oriented in other ways or move in other directions. Therefore, the terms do not limit the scope of the current technology.

Embodiments of the present technology relate to an electronic fitness device that may be worn on a user's wrist, such as the wrist-worn electronic device shown in FIG. 1A, and provides optical cardiac monitoring by generating and utilizing photoplethysmogram (PPG) signals. The electronic device may identify one or more signal paths having an acceptable signal quality metric, such as signal-to-noise ratio (SNR), for determining physiological information about the user, such as measuring a user's pulse or heart rate, a pulse oximetry ("Pulse Ox") level (also known as a level of blood oxygen saturation, or SpO2), an estimated stress level, a maximum rate of oxygen consumption (VO2 max), or the like. The electronic fitness device includes a first optical transmitter array and a second optical transmitter array, each of which is configured to output optical signals having a plurality of wavelengths. The optical signals pass through the user's skin and are received once they exit the user's skin by a plurality of optical receivers. Each optical receiver generates an electronic PPG signal for each optical signal received. The PPG signals are communicated to a processor which processes the PPG signals to determine the user's heart rate or pulse oximetry.

The wrist-worn electronic device can comprise a housing including a bottom wall configured to contact a user's wrist, an optical transmitter and receiver assembly and a processor. A band can attach the housing of the wrist-worn electronic device to a wrist of a user. The wrist-worn electronic device may be a fitness watch, a wrist-worn smart phone, a wrist-worn navigation device, or other wearable multi-function electronic devices that include a housing and a wrist band, strap, or other attachment mechanism. Although the wrist-worn electronic device is typically worn on a wrist, it may also be worn on other parts of the body such as an extremity, the forearm or the upper arm.

The optical cardiac monitor broadly comprises a housing, a first optical transmitter, a first optical receiver, a second optical transmitter, and a second optical receiver. The housing includes a bottom wall configured to contact a user's wrist and one or more side walls substantially perpendicular to an arm axis that passes from the user's elbow to the user's hand of that arm. The first optical transmitter is positioned at a first location on the bottom wall and is operable to output a first optical signal that passes through a user's skin. The first optical receiver is positioned at a second location on the bottom wall and is operable to receive the first optical signal from the first optical transmitter such that the optical signals travel along a first signal path from the first optical transmitter to the first optical receiver. The first signal path from the first location to the second location is substantially parallel to the arm axis of the user. The second optical transmitter is positioned at a third location on the bottom wall and is operable to output a second optical signal that passes through a user's skin. The second optical receiver is positioned at a fourth location on the bottom wall and is operable to receive the second optical signal from the second optical transmitter such that the optical signals travel along a second signal path from the second optical transmitter to the second optical receiver. The second path from the third location to the fourth location is also substantially parallel to the arm axis of the user. Therefore, the first signal path and the second signal path are both substantially parallel to the arm axis that passes from the user's elbow to the user's hand of that arm, which results in one of the signal paths being closer to the ulna bone in the user's wrist and the other signal being closer to the radius bone in the user's wrist.

Ligaments and/or bones in a wrist generally, referred to herein as wrist structures, run substantially parallel to an arm axis as such wrist structures extend from the user's elbow to the user's hand through the user's wrist. Conventional optical cardiac monitors often include a plurality signal paths between optical transmitters and optical receivers. For instance, the signal paths may run substantially diagonal to or perpendicular to the arm axis, which can result in a number of signal paths extending from optical transmitters to optical receivers that are adjacent to and/or crossing wrist structures. The presence of wrist structures can adversely impact the determination of physiological information such as a user's heart rate and pulse oximetry by reducing a signal-to-noise ratio for the optical signals that pass through the wrist at or proximate to the location of such wrist structure.

Conventional optical cardiac monitors that have a plurality of signal paths often do not have two or more signal paths that are substantially parallel to a user's wrist structures. As there are many environmental considerations that may impact the signal quality metric, such as the signal-to-noise ratio, of the PPG signals that are generated by optical receivers (photodiodes) based on received optical signals that have passed from an optical transmitter to an optical receiver, optical signals that pass through a signal path that either cross wrist structure or are substantially adjacent to the wrist structures may have a lower signal quality metric, such as signal-to-noise ratio, than optical signals that do not cross wrist structure and are not proximate to wrist structures.

In embodiments, the wrist-worn electronic device optical cardiac monitor includes a plurality of optical transmitters and a plurality of optical receivers forming two or more signal paths that are oriented to be substantially parallel to an arm axis when the wrist-worn electronic device is worn by a user. As the two or more signal paths are substantially parallel to the arm axis, which may substantially correspond to the direction of many wrist structures, the signal paths extending from optical transmitters to optical receivers are less likely to cross wrist structures.

In various embodiments, the two or more signal paths substantially parallel to the arm axis may be colinear with a wrist structure. Accordingly, the wrist-worn electronic device disclosed herein includes a plurality of signal paths from optical transmitters to optical receivers to increase the probability that at least one signal path does not pass through (intersect) or near a wrist structure and the processing is configured to select one or more PPG signals generated by optical receivers corresponding to the plurality of signal paths to determine accurate physiological information for the user in real-time.

Optical signals having different wavelengths are capable of penetrating or reaching different regions of the user's skin and tissue. In some embodiments, each optical transmitter 108 may include a photonic generator, such as a light-emitting diode (LED), a modulator, a top emitter, an edge emitter, or the like. The photonic generator receives an electrical input signal from the processor 120 that may be a control signal, such as an electric voltage or electric current that is analog or digital, or data, either of which is indicative of activating or energizing the optical transmitter 108 to output an optical signal having a desired amplitude, frequency, and duration. The photonic generator of each optical transmitter 108 transmits or outputs electromagnetic radiation having a particular wavelength (the optical signal) in the visible light spectrum, which is typically between approximately 400 nanometers (nm) to 700 nm, or in the near infrared spectrum, which is typically between approximately 700 nm to 1,000 nm. In some embodiments, the photonic generator transmits electromagnetic radiation in a wavelength range of 1,000 nm to 1,500 nm. The wavelength of the optical signal is generally determined by, or varies according to, the material from which the photonic generator of each optical transmitter 108 is formed. The optical signal may comprise a sequence of pulses, a periodic or non-periodic waveform, a constant level for a given period of time, or the like, or combinations thereof. In other embodiments, each optical transmitter 108 may include a driver circuit, with electronic circuitry such as amplifier and an optional filter, electrically coupled to the photonic generator. The driver circuit may receive the electrical input signal (control signal) from the processor 120 and the driver circuit may generate an electric voltage or electric current to the photonic generator, which in turn, outputs the optical signal.

Figure 1B:
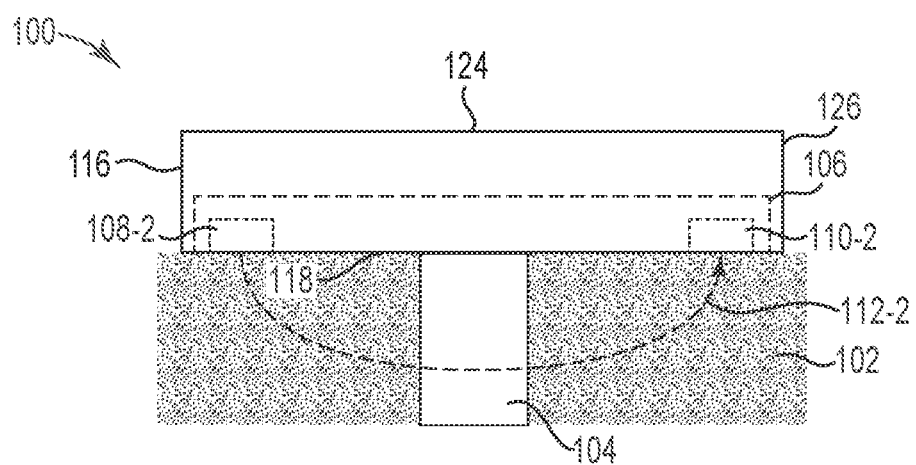
FIG. 1B illustrates a side view of a wrist-worn electronic device.
Figure 1C:
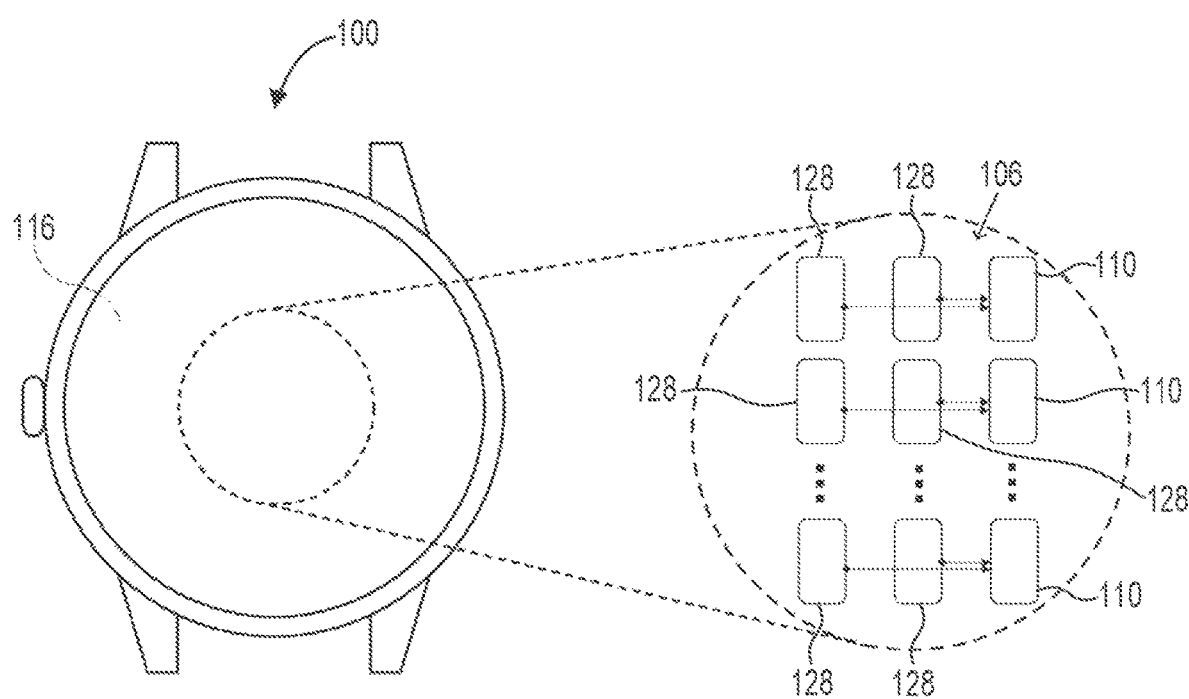
FIG. 1C is a bottom view of the wrist-worn electronic device, illustrating a plurality of optical transmitter arrays and a plurality of optical receivers.

FIG. 1A illustrates a top view of a wrist-worn electronic device 100 in a wrist and a hand region of a user 102, FIG. 1B illustrates a side view of the wrist-worn electronic device 100 and FIG. 1C a bottom view of the wrist-worn electronic device 100, illustrating a plurality of optical transmitter arrays 128 and a plurality of optical receivers 110. The wrist-worn electronic device 100 includes a housing 116, which includes a bottom wall 118 incorporating an optical transmitter and receiver assembly 106, and a wrist band 104 to attach the wrist-worn electronic device 100 to a wrist of the user 102. The wrist-worn electronic device includes a processor 120 and a memory element 122, the processor 120 configured to determine physiological information about the user, such as the user's heart rate and pulse oximetry.

The housing 116 generally houses or retains other components of the wrist-worn electronic device 100 and may include or be coupled to the wrist band 104. As seen in FIG. 1B, housing 116 may include a bottom wall 118, an upper surface 124, and at least one side wall 126 that bound an internal cavity (not shown in the figures). The bottom wall 118 includes a lower, outer surface that contacts the user's wrist while the user is wearing the wrist-worn electronic device 100. The bottom wall 118 may be substantially flat with a slight curvature that enables the bottom wall 118 to contact a substantial portion of the user's upper wrist. The upper surface 124 opposes the bottom wall 118. In various embodiments, the upper surface 124 may further include an opening that extends from the upper surface 124 to the internal cavity. In some embodiments, such as the exemplary embodiments shown in the figures, the bottom wall 118 of housing 116 may have a round, circular, or oval shape, with a single circumferential side wall 126. In other embodiments, the bottom wall 118 may have a four-sided shape, such as a square or rectangle, or other polygonal shape, with the housing 116 including four or more sidewalls. As seen in FIG. 1C, bottom wall 118 of the housing 116 may include one or more openings in which a plurality of optical transmitter arrays 128, at least some of which include a plurality of optical transmitters 108, and the optical receivers 110 are placed, positioned, or located. The one or more openings within the bottom wall 118 of the housing 116 may be covered by one or more lenses through which the optical signals may be transmitted and received.

The optical transmitter and receiver assembly 106 is located at a bottom wall 118 of the wrist-worn electronic device 100 such that it is positioned adjacent to skin of the user 102 when the housing 116 is secured to the user's wrist by wrist band 104. The optical transmitter and receiver assembly 106 includes a plurality of optical transmitters 108 and a plurality of optical receivers 110. The optical transmitter and receiver assembly 106, optical transmitters 108, and optical receivers 110 are each depicted in FIGS. 1A-1B by dashed lines because the optical transmitter and receiver assembly 106, optical transmitters 108, and optical receivers 110 are positioned within and/or at the bottom wall 118 of the wrist-worn electronic device 100.

In FIG. 1A, two of the plurality of optical transmitters and two of the plurality of optical receivers are depicted. A first optical transmitter 108-1 is positioned at a first location on the bottom wall 118 and is operable to output a first optical signal that passes through a user's skin. The first optical receiver 110-1 is positioned at a second location on the bottom wall 118 and is operable to receive the first optical signal from the first optical transmitter 108-1 such that the optical signals travel along a first signal path 112-1 from the first optical transmitter 108-1 to the first optical receiver 110-1. The first signal path 112-1 from the first location to the second location is substantially parallel to the arm axis 101 of the user 102.

The first optical signal is reflected from the upper layers of skin of the user 102 towards the first optical receiver 110-1 along the first signal path 112-1. Similarly, a second optical signal is output from the second optical transmitter 108-2 and reflected from the upper layers of skin of the user 102 towards a second optical receiver 110-2 along a second signal path 112-2. The first optical receiver 110-1 measures an intensity of the first optical signal and generates a first PPG signal corresponding to the measured intensity of the first optical signal and the second optical receiver 110-2 measures an intensity of the second optical signal and generates a second PPG signal corresponding to the measured intensity of the second optical signal. The intensity of the first optical signal and the second optical signal varies in accordance with the amount of blood in the regions of the user's tissue in the first and second signal paths 112-1, 112-2 and changes as the blood is moved through the body of the user 102 with each heartbeat. The changing levels of blood in the tissue of the skin of the user 102 proximate to the optical transmitter and receiver assembly 106 along the first and second signal paths 112-1, 112-2 results in different intensity of the first and second optical signals, respectively. Accordingly, a processor can determine physiological information for the user 102 based on the first PPG signal, the second PPG signal, or a combination thereof.

The first optical receiver 110-1 is separated from the first optical transmitter 108-1 such that the first optical signal transmitted from (output by) the first optical transmitter 108-1 travels along signal path 112-1, which is substantially parallel to the arm axis 101 of the user 102, to the first optical receiver 110-1. The arm axis 101 extends along a portion of a length of an arm of the user 102 from an elbow to a hand of that arm. The second optical receiver 110-2 is separated from the second optical transmitter 108-2 such that the second optical signal transmitted from (output by) the second optical transmitter 108-2 travels along signal path 112-2, which is substantially parallel to the arm axis 101 of the user 102, to the second optical receiver 110-2. Signal paths 112-1, 112-2 are each depicted in FIG. 1 using dashed lines because the signal paths 112-1, 112-2 are within the upper layers of skin tissue of the user 102 under the bottom wall 118 of the wrist-worn electronic device 100 when the wrist-worn electronic device 100 is worn by the user 102.

In embodiments, a first lens is positioned along bottom wall 118 at the first location over the first optical transmitter 108-1 and a second lens is positioned along bottom wall 118 at the second location over the second optical transmitter 108-2. In such embodiments, if a plurality of first optical signals are output by the first optical transmitter 108-1, the plurality of first optical signals pass through the first lens and are received by the first optical receiver 110-1. Similarly, if a plurality of second optical signals are output by the second optical transmitter 108-2, the plurality of second optical signals pass through the second lens and are received by the second optical receiver 110-2.

FIG. 1B illustrates one of the plurality of signal paths that are substantially parallel to arm axis 101. Similar to the first optical signal, the second optical signal is output by the second optical transmitter 108-2 and travels through the skin of the user 102 along signal path 112-2 to the second optical receiver 110-2.

Wrist structures 114, such as bones, muscle ligaments or tendons, nerves and other structures, typically have properties that substantially differ from properties of the blood vessels and skin tissue through which blood moves through the wrist of the user 102. A plurality of exemplary wrist structures 114-1, 114-2 and 114-3 are depicted in FIG. 1A and each wrist structure 114-1, 114-2, 114-3 is represented by a respective pair of dashed lines for ease of illustration. Actual biological wrist structures 114 may not be entirely parallel to the arm axis 101 or have a uniform structure or path within the wrist under the bottom wall 118 or the portion of the hand that is proximate to the housing 116. The wrist structures 114 can be relatively dense and can compress soft dermal tissue, which may impact any optical signals that travel from an optical transmitter 108 to an optical receiver 110 along signal paths 112-1, 112-2. Additionally, the wrist-worn electronic device 100 may exert a force compressing soft tissue against such wrist structures 114 when worn and movement of wrist structures 114 caused by, for example, movement of fingers may impact any optical signals that travel along signal paths 112-1, 112-2. The presence of wrist structures 114 along either signal paths 112-1 or signal path 112-2, thus may introduce noise to a PPG signal generated by an optical receiver 110 based on the optical signals that passed along signal paths 112-1, 112-2.

As illustrated in FIG. 1A, wrist structures 114-1, 114-2, 114-3, which may be bones, muscle ligaments or tendons, nerves and other structure, generally include one or more portions that are substantially parallel to the arm axis 101. In embodiments, the wrist-worn electronic device 100 includes an optical transmitter and receiver assembly 106 including optical transmitters 108 and optical receiver 110 that output and receive optical signals, respectively, that pass along signal paths 112-1, 112-2, which are substantially parallel to arm axis 101. For many users 102, one or more wrist structures 114-1, 114-2, 114-3 may not exist along one or both of signal paths 112-1 or 112-2. For many users 102, it is desirable for a processor to determine physiological information about the user 102 based on PPG signals corresponding to optical signals that pass along signal paths 112-1, 112-2 that are not proximate to (i.e., located away from) any of wrist structures 114-1, 114-2, 114-3 as the tissue that the optical signals will have passed through are less likely to have been influenced by the presence of wrist structures 114-1, 114-2, 114-3 or pressure resulting from wrist structures 114-1, 114-2, 114-3. Consequently, in embodiments of the present invention, the processor may be configured to determine whether a PPG signal generated by an optical receiver 110 corresponds to an optical signal that passed along a signal path 112-1 or 112-2 that did not contain noise caused by substantial wrist structures 114-1, 114-2, 114-3 along signal paths 112-1, 112-2 as such PPG signals would be determined to have a higher signal quality metric (e.g., signal-to-noise ratio) than other PPG signals. As a result, the configuration and techniques disclosed herein enable accurate determination of physiological information for a user 102.

Although only two signal paths 112-1, 112-2 are shown in FIG. 1A, it is to be understood that an optical transmitter and receiver assembly 106 of the wrist-worn electronic device 100 can include sufficient optical transmitters 108 and optical receivers 110 that would result in three or more signal paths 112 along which optical signals pass through the wrist of the user 102. For instance, as shown in FIG. 1A, the optical transmitter and receiver assembly 106 may include two optical transmitters 108-1, 108-2 and two optical receivers 110-1, 110-2 resulting in optical signals passing along signal paths 112-1, 112-2 substantially parallel to arm axis 101 and one or both of signal paths 112-1, 112-2 may be separated from and possibly colinear with one or more of wrist structures 114-1, 114-2, 114-3 present in the wrist of the user 102.

In some cases, a user 102 may have over-tightened wrist band 104 when securing the housing 116 to the wrist of the user 102 as many users mistakenly believe fastening the wrist band 104 as tight as possible or tolerable improves the accuracy of physiological information determined by the processor for the user 102. However, for many users 102, an overly-tightened wrist band 104 can result in the pressure applied by the housing 116 and wrist band 104 against and around the wrist of the user 102 pinching tissue against one or more wrist structure 114. As the blood vessels in the extremity are positioned amongst and between ligaments, bones and tissue, compression of the extremity typically causes the blood vessels to be compressed by adjacent ligaments, bones and tissue and, eventually, such compression leads to a narrowing (in diameter, when measured at a cross-section) or occlusion of the blood vessels. As blood vessels compress far more than ligaments and bones, a device that is worn unnecessarily tight may narrow the blood vessels as the area is compressed more than necessary for the device to accurately determine cardiac information. Accordingly, there is an ideal range of pressure that is applied to the wrist of the user that enables the optical signals output by an optical transmitter 108 to pass through the skin tissue to an optical receiver 110 with a high signal quality metric, such as signal-to-noise ratio.

In some cases, excessive or unnecessarily-high pressure levels of the housing 116 against the wrist of the user 102 can cause movement of wrist structure 114, which can include movement of an otherwise non-obstructing wrist structure 114-1 to be present along signal path 112-1. In such an event, the first optical receiver 110-1 would receive the first optical signal after it has passed along obstructed signal path 112-1 and output a PPG signal having a lower signal quality metric, such as signal-to-noise ratio, than a PPG signal that could have been generated had the first optical signal passed through a substantially unobstructed signal path 112-1 due to various factors, such as degradation of the first optical signal and scattering of the first optical signal off of an obstructing wrist structure 114-1.

To increase the accuracy of physiological information determined by the wrist-worn electronic device 100, the optical transmitter and receiver assembly 106 can include a plurality of signal paths, such as substantially parallel first and second signal paths 112-1, 112-2. The location of optical transmitters 108 and optical receiver 110 of the optical transmitter and receiver assembly 106 resulting in two or more substantially parallel signal paths 112 enables the processor to identify and select at least one of the PPG signals associated with the plurality of signal paths 112 that may be least obstructed by wrist structures 114 and determine accurate physiological information for the user 102 based on the selected PPG signals in real-time. In some embodiments, more than half of the optical transmitters 108 and optical receivers 110 of the optical transmitter and receiver assembly 106 resulting in the two or more substantially parallel signal paths 112 may be located towards one side of the bottom wall 118 of the housing 116 as the housing 116 may be oriented when worn such that the side having more of the optical transmitters 108 and optical receivers 110 align with a thumb side of a wrist of the user 102 because that portion of the wrist typically has fewer wrist structures 114-1, 114-2, 114-2 than the opposing portion (pinky finger side) of the wrist of the user 102.

As in FIG. 1A, multiple optical transmitter and optical receiver pairs are arranged such that the signal paths 112-1, 112-2 between them are substantially parallel. For instance, housing 116 may be secured to the user's wrist such that signal paths 112 are oriented substantially parallel to the arm axis (extending along a portion of the length of the arm from the user's elbow to his or her hand). In this configuration, one or more signal paths 112 may overlap wrist structure 114, such as bones, muscle ligaments or tendons, nerves and other structure, but one or more signal paths 112 may be substantially away from any wrist structure 114 and any such signal paths 112 that are not proximate to wrist structure 114 may be utilized or weighted by the processor 120 to determine physiological information for the user as such signal paths 112 may be less impacted from pressure modulation by wrist structure 114 and include less noise induced by wrist structure 114 than a signal path 112 in proximity to wrist structure 114. Consequently, when housing 116 is secured to a user's wrist, the sensor geometry shown in FIG. 1A is more likely to include a signal path 112 with high signal quality than conventional geometries or layouts of optical transmitter and receiver assemblies.

Figure 2:
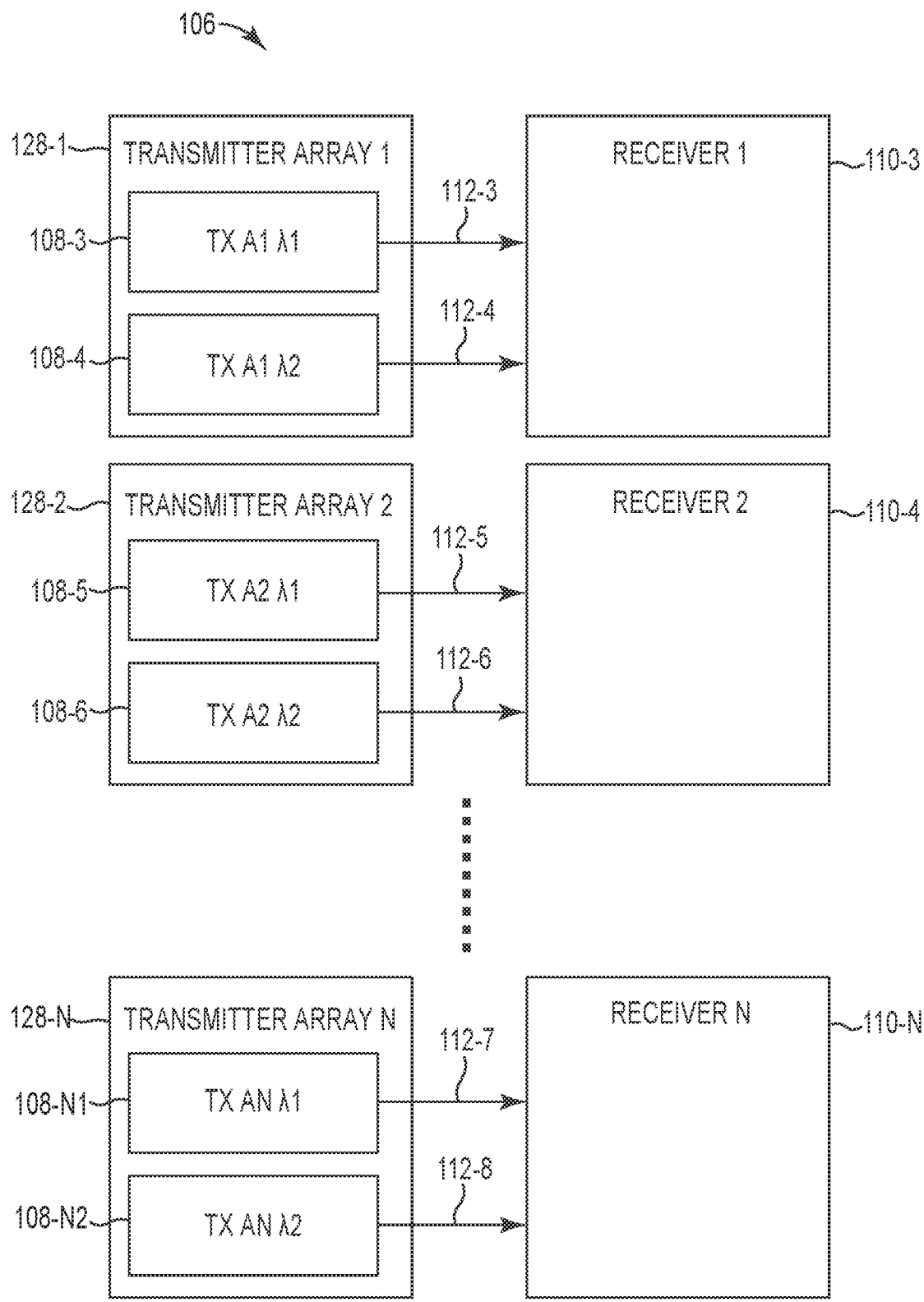
FIG. 2 is a schematic view of a first embodiment of a plurality of optical transmitter arrays and optical receivers illustrating pathways of the optical signal transmitted by each of the optical transmitters and received by one of a plurality of optical receivers of a wrist-worn electronic device.

FIG. 2 is a schematic view of a first embodiment of an optical transmitter and receiver assembly 106 having a plurality of optical transmitter arrays 128 and optical receivers 110 illustrating signal paths of the optical signal transmitted by each of the optical transmitters 108 and received by one of a plurality of optical receivers 110. The optical transmitter and receiver assembly 106 includes a plurality of optical transmitter arrays 128-1, 128-2, 128-N and a plurality of corresponding optical receivers 110-3, 110-4, 110-N. Each optical transmitter array 128 includes a plurality of optical transmitters 108 in the same packaging. For example, the first optical transmitter array 128-1 includes a first optical transmitter 108-3 (TX A1 $\lambda$1) and a second optical transmitter 108-4 (TX A1 $\lambda$2), the second optical transmitter array 128-2 includes a first optical transmitter 108-5 (TX A2 $\lambda$1) and a second optical transmitter 108-6 (TX A2 $\lambda$2), and an Nth optical transmitter array 128-N includes a first optical transmitter 108-N1 (TX AN $\lambda$1) and a second optical transmitter 108-N2 (TX AN $\lambda$2).

The first optical transmitter 108-3 (TX A1 $\lambda$1) of the first optical transmitter array 128-1 is configured to output (emit) a first optical signal having a first wavelength and the second optical transmitter 108-4 (TX A1 $\lambda$2) of the first optical transmitter array 128-1 is configured to output (emit) a second optical signal having a second wavelength. The first optical receiver 110-3 (Receiver 1) is positioned at a location on the bottom wall 118 of the housing 116 that is separated from the first optical transmitter 108-3 (TX A1 $\lambda$1) of the first optical transmitter array 128-1 such that the first optical signal output by the first optical transmitter 108-3 (TX A1 $\lambda$1) travels along a first signal path 112-3, which is substantially parallel to an arm axis of a user, such as arm axis 101 depicted in FIG. 1A, from the first optical transmitter 108-3 (TX A1 $\lambda$1) to first optical receiver 110-3 (Receiver 1). The location of the first optical receiver 110-3 (Receiver 1) is also separated from second optical transmitter 108-4 (TX A1 $\lambda$2) such that the second optical signal output by second optical transmitter 108-4 (TX A1 $\lambda$2) travels along a second signal path 112-4, which is substantially parallel to the arm axis of the user from transmitter 108-4 (TX A1 $\lambda$2) to the first optical receiver 110-3 (Receiver 1). In some embodiments, the processor is configured to control the first optical transmitter 108-3 (TX A1 $\lambda$1) and the second optical transmitter 108-4 (TX A1 $\lambda$2) to output the first optical signal and the second optical signal, respectively, at predetermined times, which may cause the first and second optical signals to be transmitted sequentially, simultaneously or during partially overlapping times. As illustrated in FIG. 2, the locations of the first optical transmitter 108-3 (TX A1 $\lambda$1) and the second optical transmitter 108-4 (TX A1 $\lambda$2) on the bottom wall 118 of the housing 116 may result in substantially non-overlapping signal paths 112-3, 112-4 to the first optical receiver (Receiver 1).

The first optical transmitter 108-5 (TX A2 $\lambda$1) of the second optical transmitter array 128-2 is configured to output (emit) a third optical signal having a first wavelength and the second optical transmitter 108-6 (TX A2 $\lambda$2) of the second optical array 128-2 is configured to output (emit) a fourth optical signal having a second wavelength. The first optical receiver 110-3 (Receiver 1) is positioned at a location on the bottom wall 118 of the housing 116 that is separated from the first optical transmitter 108-5 (TX A2 $\lambda$1) of the second optical transmitter array 128-2 such that the third optical signal output by the first optical transmitter 108-5 (TX A2 $\lambda$1) travels along a first signal path 112-5, which is substantially parallel to an arm axis of a user, such as arm axis 101 depicted in FIG. 1A, from the first optical transmitter 108-5 (TX A2 $\lambda$1) to the second optical receiver 110-4 (Receiver 2). The location of the second optical receiver 110-4 (Receiver 2) is also separated from second optical transmitter 108-6 such that the fourth optical signal output by second optical transmitter 108-6 (TX A2 $\lambda$2) travels along a second signal path 112-4, which is substantially parallel to the arm axis of the user from optical transmitter 108-6 (TX A2 $\lambda$2) to the second optical receiver 110-4 (Receiver 2). In some embodiments, the processor is configured to control the first optical transmitter 108-5 (TX A2 $\lambda$1) and the second optical transmitter 108-6 (TX A2 $\lambda$2 to output the third optical signal and the fourth optical signal, respectively, at predetermined times, which may cause the third and fourth optical signals to be transmitted sequentially, simultaneously or during partially overlapping times. As illustrated in FIG. 2, the locations of the first optical transmitter 108-5 (TX A2 $\lambda$1) and the second optical transmitter 108-6 (TX A2 $\lambda$2) on the bottom wall 118 of the housing 116 may result in substantially non-overlapping signal paths 112-5, 112-6 to the second optical receiver (Receiver 2).

The first optical transmitter 108-N1 (TX AN $\lambda$1) of the Nth optical transmitter array 128-N is configured to output (emit) an optical signal having a first wavelength and the second optical transmitter 108-N2 (TX AN $\lambda$2) of the Nth optical transmitter array 128-N is configured to output (emit) an optical signal having a second wavelength. The Nth optical receiver 110-N (Receiver N) is positioned at a location on the bottom wall 118 of the housing 116 that is separated from the first optical transmitter 108-N1 (TX AN $\lambda$1) of the Nth optical transmitter array 128-N such that the optical signal output by the first optical transmitter 108-N1 (TX AN $\lambda$1) travels along a first signal path 112-7, which is substantially parallel to an arm axis of a user, such as arm axis 101 depicted in FIG. 1A, from the first optical transmitter 108-N1 (TX AN $\lambda$1) to the Nth optical receiver 110-N (Receiver N). The location of the Nth optical receiver 110-N (Receiver N) is also separated from first optical transmitter 108-N1 (TX AN $\lambda$1) such that the optical signal output by second optical transmitter 108-N2 (TX AN $\lambda$2) travels along a second signal path 112-8, which is substantially parallel to the arm axis of the user from optical transmitter 108-N2 (TX AN $\lambda$2) to the Nth optical receiver 110-N (Receiver N). In some embodiments, the processor is configured to control the first optical transmitter 108-N1 (TX AN $\lambda$1) and the second optical transmitter 108-N2 (TX AN $\lambda$2) to output the optical signal by each at predetermined times, which may cause the optical signals to be transmitted sequentially, simultaneously or during partially overlapping times. As illustrated in FIG. 2, the locations of the first optical transmitter 108-N1 (TX AN $\lambda$1) and the second optical transmitter 108-6 (TX AN $\lambda$2) on the bottom wall 118 of the housing 116 may result in substantially non-overlapping (common) signal paths 112-7, 112-8 to the Nth optical receiver (Receiver N).

Although the Figures depict each optical transmitter array 128 having only two optical transmitters 108, it is to be understood that each optical transmitter array 128 may incorporate additional optical transmitters 108 in order to output (emit) optical signals at wavelengths other than the first wavelength and the second wavelength. Accordingly, an exemplary first optical transmitter array 128-1 may include a first optical transmitter 108-3 (TX A1 λ1) configured or operable to output an optical signal having a first wavelength (λ1), a second optical transmitter 108-4 (TX A1 λ2) configured or operable to output an optical signal having a second wavelength (λ2 and a third optical transmitter configured or operable to output an optical signal having a third wavelength (λ3). In embodiments, the first wavelength (λ1) may range from approximately 600 nm to approximately 680 nm, the second wavelength (λ2) may range from approximately 680 nm to approximately 750 nm and the third wavelength (λ3) may range from approximately 750 nm to approximately 950 nm. In other embodiments, the first wavelength (λ1) may range from approximately 630 nm to approximately 700 nm, the second wavelength (λ2) may range from approximately 700 nm to approximately 780 nm and the third wavelength (λ3) may range from approximately 780 nm to approximately 900 nm. In some embodiments, the third wavelength (λ3) may range from approximately 900 nm to approximately 1,025 nm. Two or more of the PPG signals associated with these wavelengths may be utilized in combination to determine the user's pulse oximetry, heartrate or hemoglobin levels of various forms such as methemoglobin, carboxyhemoglobin, glycated hemoglobin or sulfhemoglobin.

Similar to signal paths 112-1 and 112-2 shown in FIG. 1B, signal paths 112-3, 112-4, 112-5, 112-6, 112-7, 112-8 are also formed within and pass through the skin tissue of a wrist of the user 102 around which the housing 116 is secured using wrist band 104. Within the tissue, the optical signals encounter permanent and/or pulsatile cardiovascular wrist structures such as arterioles and capillaries through which the optical signals modulate and pass through to an optical receiver, which generates a PPG signal that is associated with its signal path 112.

Human skin tissue is not homogeneous and the presence of pulsating cardiovascular wrist structures differs between different areas of the skin tissue. Thus, two signal paths such as signal path 112-3 and signal path 112-4 may differ in effective optical signal path length even though the optical transmitter for each is separated from the respective optical sensor by an equal length. Furthermore, various conditions and processes in human skin continuously vary the average volume of blood in cardiovascular wrist structures in response to a range of environmental and physiological variables.

Each optical array 128 may contain a plurality of optical transmitters 108 that are substantially equidistant to an optical receiver 110. For instance, the first optical transmitter 108-3 (TX A1 λ1) and the second optical transmitter 108-4 (TX A1 λ2) within the first optical transmitter array 128-1 may be positioned adjacent to one another and signal paths 112-3, 112-4 to the first optical receiver 110-3 (Receiver 1) may substantially overlap in the sensing (e.g., skin) plane.

Figure 3A:
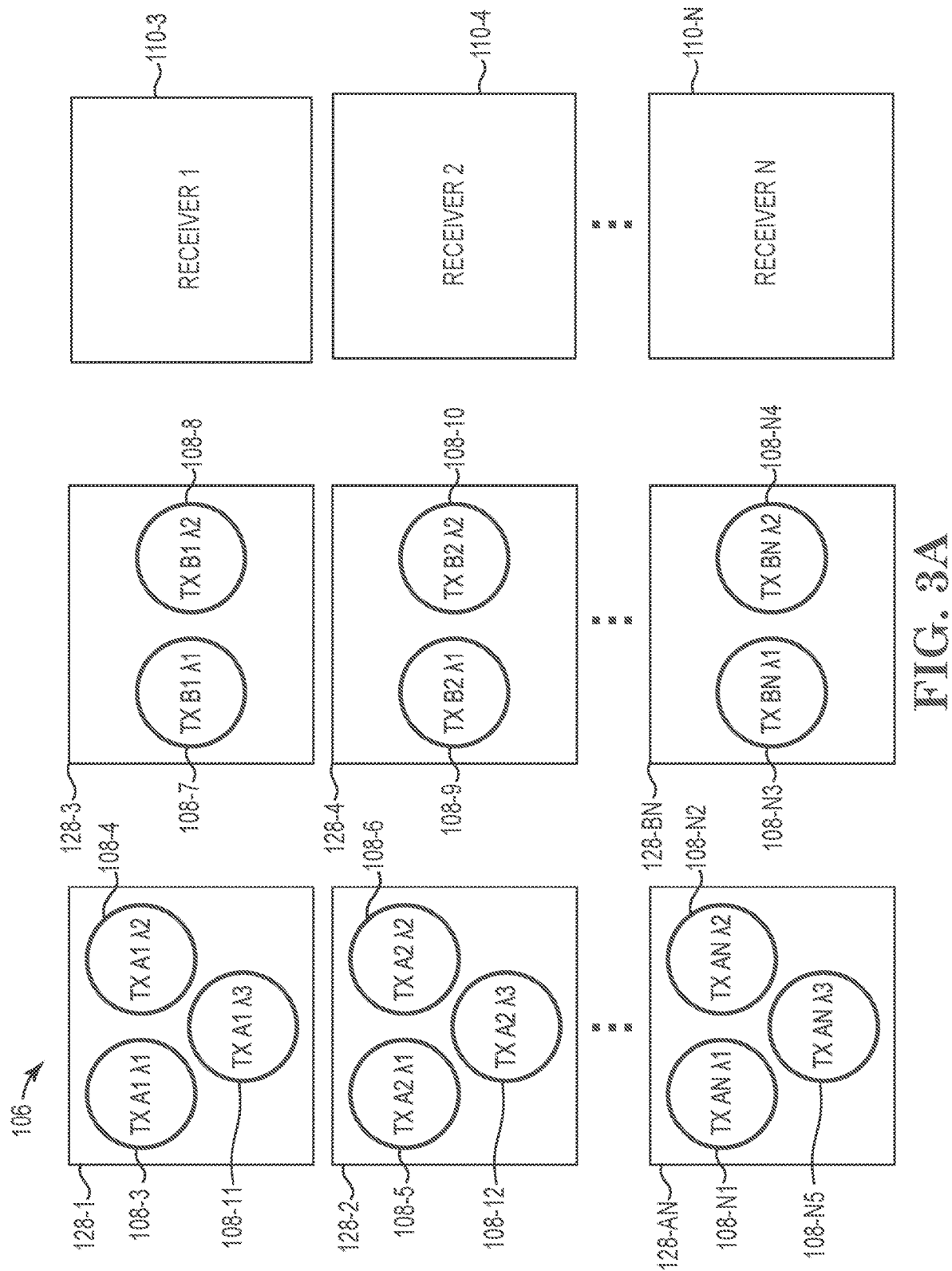
FIG. 3A is a schematic view of a second embodiment of the plurality of optical transmitter arrays and optical receivers of the wrist-worn electronic device.
Figure 3B:
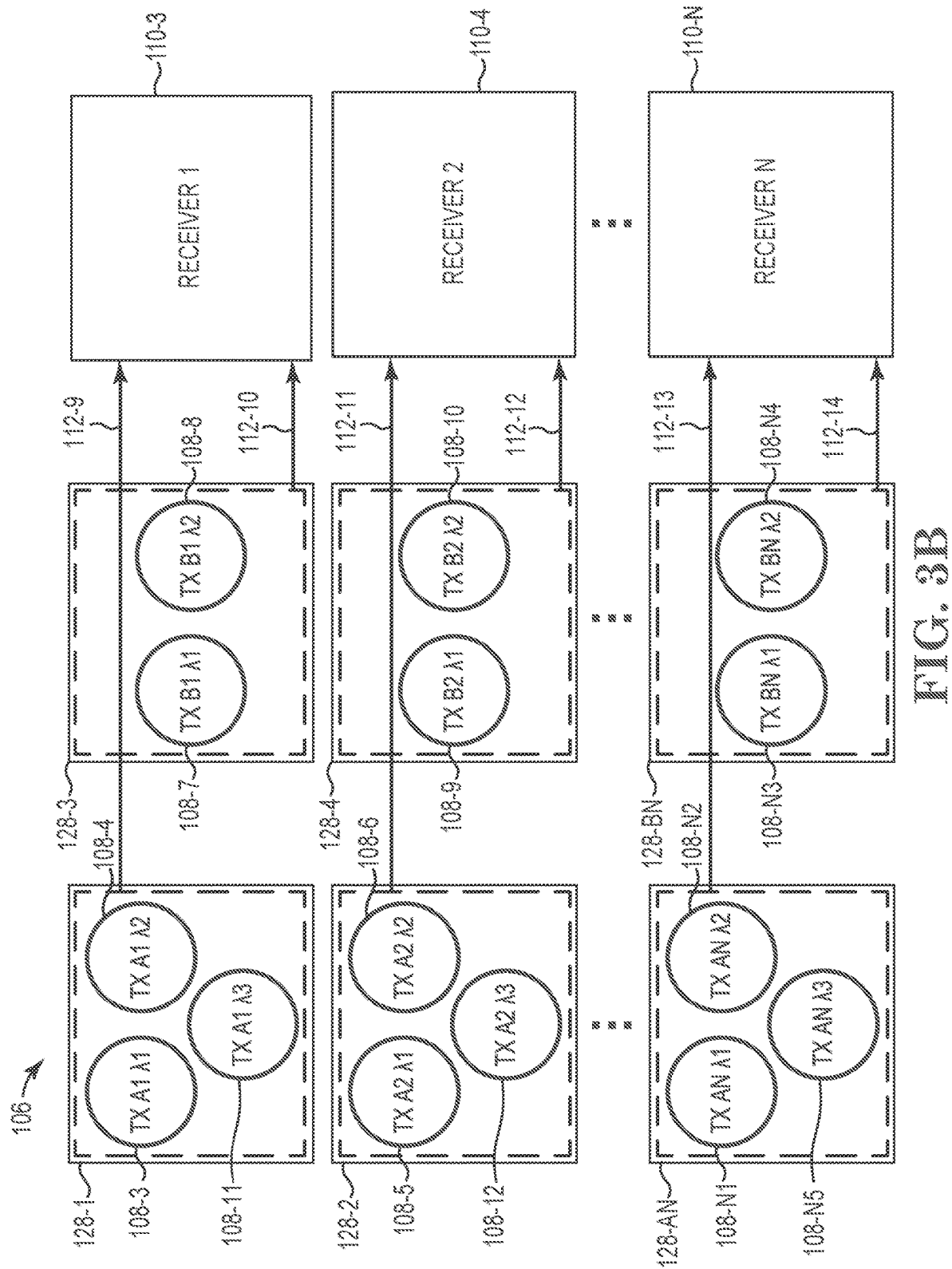
FIG. 3B is a schematic view of the second embodiment of the plurality of optical transmitter arrays and optical receivers of the wrist-worn electronic device illustrating pathways of the optical signal transmitted by each of the optical transmitters and received by one of a plurality of optical receivers of a wrist-worn electronic device.

FIG. 3A is a schematic view of a second embodiment of an optical transmitter and receiver assembly 106 having a plurality of optical transmitter arrays 128 arranged relative to each optical receiver 110 such that a plurality of optical signals received by each optical receiver 110 travel along the same or a substantially overlapping (common) signal path. As shown in FIG. 3A, each optical receiver 110 is configured to receive optical signals output by two optical transmitter arrays 128. FIG. 3B is a schematic view of the second embodiment illustrating signal paths of the optical signal transmitted by each of the optical transmitters 108 and received by one of a plurality of optical receivers 110. Similar to the first embodiment depicted in FIG. 2, the optical transmitter and receiver assembly 106 depicted in FIGS. 3A and 3B includes a number of optical transmitter arrays 128-1, 128-2, 128-3, 128-4, 128-AN and 128-BN and a number of optical receivers 110-3 (Receiver 1), 110-4 (Receiver 2), 110-N (Receiver N). Although each optical transmitter array 128 in this embodiment includes a plurality of optical transmitters 108, it is to be understood that the optical transmitter arrays 128 may contain any number of optical transmitters 108, such as one optical transmitter 108. For instance, optical arrays 128-3, 128-4 and 128-BN may contain only a single optical transmitter 108. Furthermore, although each optical transmitter array 128 in this embodiment includes a plurality of physically distinct optical transmitters 108, it is to be understood that the plurality of optical transmitters 108 or a subset of the plurality of optical transmitters 108 within any optical transmitter array 128 may be a single physical transmitter 108 capable of transmitting more than one wavelength of light.

In this embodiment, the first optical transmitter array 128-1 includes a first optical transmitter 108-3 (TX A1 λ1), a second optical transmitter 108-4 (TX A1 λ2) and a third optical transmitter 108-11 (TX A1 λ3). The first optical transmitter 108-3 (TX A1 λ1) of the first optical transmitter array 128-1 is configured to output (emit) a first optical signal having a first wavelength, the second optical transmitter 108-4 (TX A1 λ2) of the first optical transmitter array 128-1 is configured to output (emit) a second optical signal having a second wavelength and the third optical transmitter 108-11 (TX A1 λ3) of the first optical transmitter array 128-1 is configured to output (emit) a third optical signal having a third wavelength. The first optical receiver 110-3 (Receiver 1) is positioned at a location on the bottom wall 118 of the housing 116 that is separated from the first optical transmitter 108-3 (TX A1 λ1), the second optical transmitter 108-4 (TX A1 λ2) and the third optical transmitter 108-11 (TX A1 λ3) of the first optical transmitter array 128-1 such that the optical signals output by the first optical transmitter array 128-1 travel along a signal path 112-9, which is substantially parallel to an arm axis of a user, such as arm axis 101 depicted in FIG. 1A, from the first optical transmitter array 128-1 to first optical receiver 110-3 (Receiver 1).

Similarly, the second optical transmitter array 128-2 includes a first optical transmitter 108-5 (TX A2 λ1), a second optical transmitter 108-6 (TX A2 λ2) and a third optical transmitter 108-12 (TX A2 λ3). The first optical transmitter 108-5 (TX A2 λ1) of the second optical transmitter array 128-2 is configured to output (emit) a first optical signal having a first wavelength, the second optical transmitter 108-6 (TX A2 λ2) of the second optical transmitter array 128-2 is configured to output (emit) a second optical signal having a second wavelength and the third optical transmitter 108-12 (TX A2 λ3) of the second optical transmitter array 128-2 is configured to output (emit) a third optical signal having a third wavelength. The second optical receiver 110-4 (Receiver 2) is positioned at a location on the bottom wall 118 of the housing 116 that is separated from the first optical transmitter 108-5 (TX A2 λ1), the second optical transmitter 108-6 (TX A2 λ2) and the third optical transmitter 108-12 (TX A2 λ3) of the second optical transmitter array 128-2 such that the optical signals output by the second optical transmitter array 128-2 travel along a signal path 112-11, which is substantially parallel to an arm axis of a user, such as arm axis 101 depicted in FIG. 1A, from the second optical transmitter array 128-2 to the second optical receiver 110-4 (Receiver 2).

A first Nth optical transmitter array 128-AN includes a first optical transmitter 108-N1 (TX AN λ1), a second optical transmitter 108-N2 (TX AN λ2) and a third optical transmitter 108-N5 (TX AN λ3). The first optical transmitter 108-N1 (TX AN λ1) of the first Nth optical transmitter array 128-AN is configured to output (emit) a first optical signal having a first wavelength, the second optical transmitter 108-N2 (TX AN λ2) of the first Nth optical transmitter array 128-AN is configured to output (emit) a second optical signal having a second wavelength and the third optical transmitter 108-N5 (TX AN λ3) of the first Nth optical transmitter array 128-AN is configured to output (emit) a third optical signal having a third wavelength. The Nth optical receiver 110-N (Receiver N) is positioned at a location on the bottom wall 118 of the housing 116 that is separated from the first optical transmitter 108-N1 (TX AN λ1), the second optical transmitter 108-N2 (TX AN λ2) and the third optical transmitter 108-N5 (TX AN λ3) of the first optical transmitter 108-N1 such that the optical signals output by the first Nth optical transmitter array 128-AN travel along a signal path 112-13, which is substantially parallel to an arm axis of a user, such as arm axis 101 depicted in FIG. 1A, from the first Nth optical transmitter array 128-AN to the Nth optical receiver 110-N (Receiver N).

In this embodiment, the third optical transmitter array 128-3 includes a first optical transmitter 108-7 (TX B1 λ1) and a second optical transmitter 108-8 (TX Bλ2). The first optical transmitter 108-7 (TX B1 λ1) of the third optical transmitter array 128-3 is configured to output (emit) a first optical signal having a first wavelength and the second optical transmitter 108-8 (TX B1 λ2) of the third optical transmitter array 128-3 is configured to output (emit) a second optical signal having a second wavelength. The first optical receiver 110-3 (Receiver 1) is positioned at a location on the bottom wall 118 of the housing 116 that is separated from the first optical transmitter 108-7 (TX B1 λ1) and the second optical transmitter 108-8 (TX Bλ2) of the third optical transmitter array 128-3 such that the optical signals output by the third optical transmitter array 128-3 travel along a signal path 112-10, which is substantially parallel to an arm axis of a user, such as arm axis 101 depicted in FIG. 1A, from the third optical transmitter array 128-3 to first optical receiver 110-3 (Receiver 1). Optical signals that pass along signal path 112-10 travel along a substantially overlapping (common) signal path to first optical receiver 110-3 (Receiver 1) as optical signals output by the first optical transmitter array 128-1 that pass along signal path 112-9.

The fourth optical transmitter array 128-4 includes a first optical transmitter 108-9 (TX B2 λ1) and a second optical transmitter 108-10 (TX B2 λ2). The first optical transmitter 108-9 (TX B2 λ1) of the fourth optical transmitter array 128-4 is configured to output (emit) a first optical signal having a first wavelength and the second optical transmitter 108-10 (TX B2 λ2) of the fourth optical transmitter array 128-4 is configured to output (emit) a second optical signal having a second wavelength. The second optical receiver 110-4 (Receiver 2) is positioned at a location on the bottom wall 118 of the housing 116 that is separated from the first optical transmitter 108-9 (TX B2 λ1) and the second optical transmitter 108-10 (TX B2 λ2) of the fourth optical transmitter array 128-4 such that the optical signals output by the fourth optical transmitter array 128-4 travel along a signal path 112-12, which is substantially parallel to an arm axis of a user, such as arm axis 101 depicted in FIG. 1A, from the fourth optical transmitter array 128-4 to second optical receiver 110-4 (Receiver 2). Optical signals that pass along signal path 112-12 travel along a substantially overlapping (common) signal path to second optical receiver 110-4 (Receiver 2) as optical signals output by the second optical transmitter array 128-2 that pass along signal path 112-11.

The second Nth optical transmitter array 128-BN includes a first optical transmitter 108-N3 (TX BN λ1) and a second optical transmitter 108-N4 (TX BN λ2). The first optical transmitter 108-N3 (TX BN λ1) of the second Nth optical transmitter array 128-BN is configured to output (emit) a first optical signal having a first wavelength and the second optical transmitter 108-N4 (TX BN λ2 of the second Nth optical transmitter array 128-BN is configured to output (emit) a second optical signal having a second wavelength. The Nth optical receiver 110-N (Receiver N) is positioned at a location on the bottom wall 118 of the housing 116 that is separated from the first optical transmitter 108-N3 (TX BN λ1) and the second optical transmitter 108-N4 (TX BN λ2) of the second Nth optical transmitter array 128-BN such that the optical signals output by the second Nth optical transmitter array 128-BN travel along a signal path 112-14, which is substantially parallel to an arm axis of a user, such as arm axis 101 depicted in FIG. 1A, from the second Nth optical transmitter array 128-BN to Nth optical receiver 110-N (Receiver N). Optical signals that pass along signal path 112-14 travel along a substantially overlapping (common) signal path to the Nth optical receiver 110-N (Receiver N) as optical signals output by the first Nth optical transmitter array 128-AN that pass along signal path 112-13.

As shown in FIGS. 3A and 3B, two or more optical transmitter arrays 128 may be positioned laterally relative to an optical receiver 110 such that optical signals output by the two more optical transmitters 108 pass along the same or a substantially overlapping (common) signal path to an optical receiver 110. For instance, a plurality of optical transmit arrays 128 positioned further from each optical receiver 110 (optical transmitter arrays 128-1, 128-2 and 128-AN) may each contain three optical transmitters 108 and a plurality of optical transmit arrays 128 positioned closer to each optical receiver 110 may each contain two optical transmitters 108. However, in other embodiments, optical arrays 128-3, 128-4 and 128-BN may contain only a single optical transmitter 108 that is configured to output (emit) an optical signal having a first wavelength.

The first optical transmitter array 128-1 and the third optical transmitter array 128-3 can be laterally positioned relative to optical receiver 110-3 (Receiver 1) to enable signal path 112-9 and signal path 112-10 to substantially overlap between the first optical transmitter array 128-1 and optical receiver 110-3 (Receiver 1). As optical transmitter array 128-1 is positioned slightly further from optical receiver 110-3 (Receiver 1) than optical transmitter array 128-3, signal path 112-9 is slightly longer than signal path 112-10. As such, the optical signals output by optical transmitter array 128-1 travel a slightly greater distance through the skin than the optical signals output by optical transmitter array 128-3. Similarly, the second optical transmitter array 128-2 and the fourth optical transmitter array 128-4 can be laterally positioned relative to optical receiver 110-4 (Receiver 2) to enable signal path 112-11 and signal path 112-12 to substantially overlap between the second optical transmitter array 128-2 and optical receiver 110-4 (Receiver 2). The first Nth optical transmitter array 128-AN and the second Nth optical transmitter array 128-BN can be laterally positioned relative to the Nth optical receiver 110-N (Receiver N) to enable signal path 112-13 and signal path 112-14 to substantially overlap between the first Nth optical transmitter array 128-AN and the Nth optical receiver 110-N (Receiver N). Overlapping signal paths 112 between each group of lateral optical transmitter arrays 128 and corresponding optical receiver 110 may enable the processor 120 reduce noise present in one or more optical signals. As previously discussed in connection with FIG. 2, minimizing spatial diversity and effective path length variability can reduce noise and/or discrepancies in PPG signals generated based on optical signals received by optical receivers 110 from each of the optical transmitter arrays 128-1, 128-2, 128-N.

In the embodiment shown in FIGS. 3A and 3B, the first wavelength (λ1) may be between approximately 600 nm and approximately 680 nm, the second wavelength (λ2) may be between approximately 680 nm and approximately 750 nm and the third wavelength (λ3) may be between approximately 750 nm and approximately 950 nm. The processor 120 may be configured to determine an oxygenation level and a heartrate of the user based on two or more PPG signals associated with these wavelengths that are generated by optical receivers 110-3 (Receiver 1), 110-4 (Receiver 2) and 110-N (Receiver N).

In some embodiments, optical transmitter arrays 128-1 through 128-BN may include a plurality of optical transmitters 108 that output optical signals having four wavelengths. For instance, optical transmitter arrays 128-1 through 128-BN may include optical transmitters 108 that output optical signals having a first wavelength in band of 630-680 nm, a second wavelength in band of 680-750 nm, a third wavelength in band of 800-900 nm, and a fourth wavelength in band of 750-950 nm. In other configurations, optical transmitter arrays 128-1 through 128-BN may include optical transmitters 108 that output optical signals having two wavelengths in band of 630-700 nm, a third wavelength in band of 700-800 nm, and a fourth wavelength in band of 900-1,025 nm.

In embodiments, optical arrays 128-3, 128-4 and 128-BN may contain only a single optical transmitter 108 having a fourth wavelength (λ4) below 600 nm, which is associated with light visual appearing the color green. The processor 120 may be configured to determine a heartrate for the user based on output optical signals having a fourth wavelength (λ4) between approximately 540 nm and approximately 580 nm.

Figure 4:
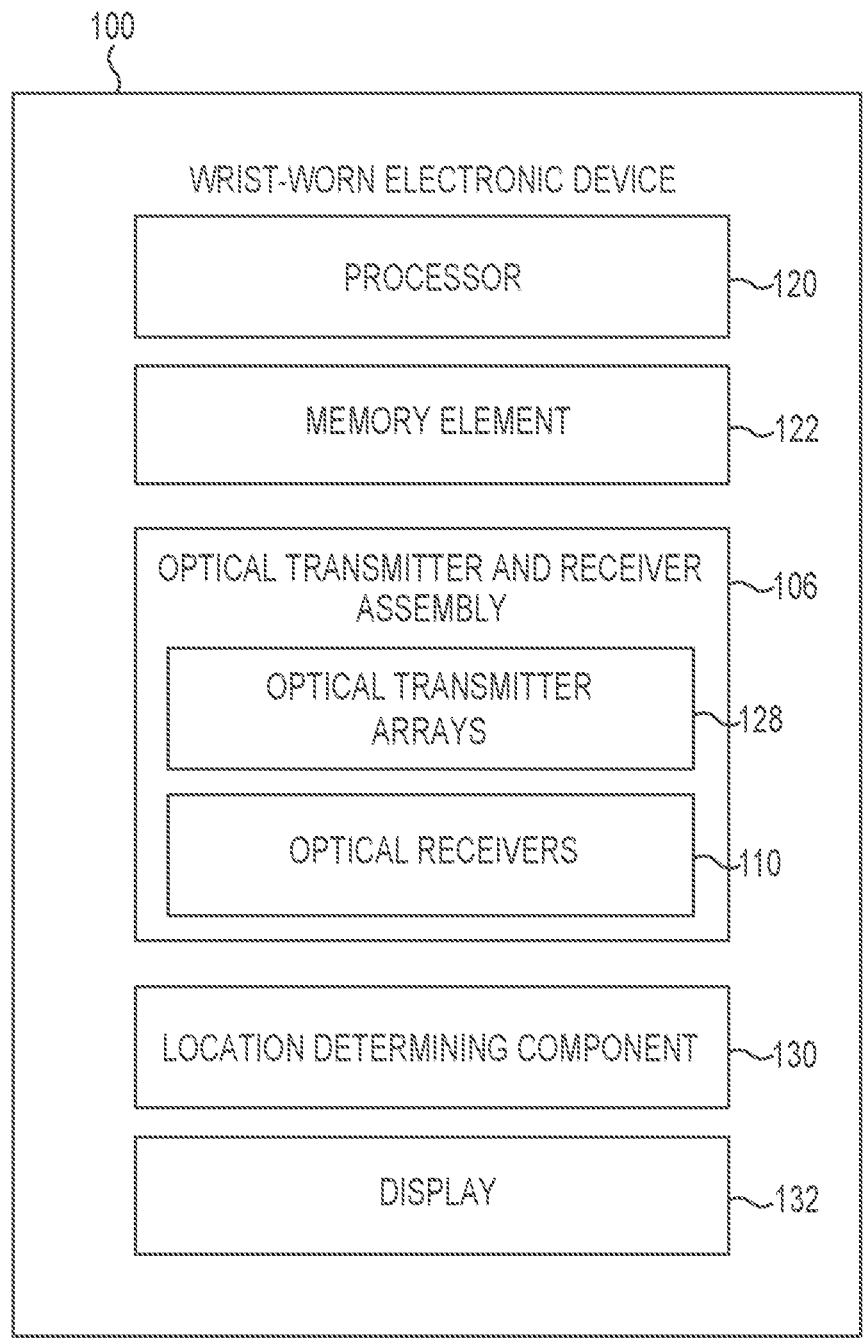
FIG. 4 is a block hardware diagram of various components of the wrist-worn electronic device.

FIG. 4 is a block diagram of a wrist-worn electronic device 100. The wrist-worn electronic device 100 includes a processor 120, a memory element 122, an optical transmitter and receiver assembly 106, a location determining component 130 and a display 132. As previously described in connection with FIGS. 1A to FIG. 3, the optical transmitter and receiver assembly 106 includes a plurality of optical transmitters 108 and a plurality of optical receivers 110.

The processor 120 provides processing functionality for the optical transmitter and receiver assembly 106 and can include any number of processors, micro-controllers, circuitry, field programmable gate array (FPGA) or other processing systems, and resident or external memory for storing data, executable code, and other information. The processor 120 is not limited by the materials from which it is formed or the processing mechanisms employed therein and, as such, can be implemented via semiconductor(s) and/or transistors (e.g., using electronic integrated circuit (IC) components), and so forth.

The processor 120 can execute one or more software programs embodied in a non-transitory computer readable medium (e.g., memory element 122) that implement techniques described herein including receiving a first PPG signal from optical receivers 110. The processor may be configured to utilize the PPG signals, which may be stored in memory element 122 or received from the optical receivers 110, to determine physiological information about the user.

In some embodiments, the processor 120 can determine a PPG signal quality metric, such as signal-to-noise ratio, of a first PPG signal and a PPG signal quality metric of a second PPG signal. The PPG signal quality metric of the first PPG signal and the PPG signal quality metric of the second PPG signal can be compared to each other and/or to a PPG signal quality metric threshold stored in memory element 122. The processor 120 may be configured to determine cardiac information for the user using the first PPG signal if the PPG signal quality metric of the first PPG signal exceeds the PPG signal quality metric threshold or the PPG signal quality metric of the second PPG signal. Similarly, the processor 120 may be configured to determine cardiac information for the user using the second PPG signal if the PPG signal quality metric of the second PPG signal exceeds the PPG signal quality metric threshold or the PPG signal quality metric of the first PPG signal.

In embodiments, the processor 120 can determine a signal quality metric of each of the first PPG signal and the second PPG signal and then compare the signal quality metric threshold stored in memory element 122 with each of the determined signal quality metric of the first PPG signal and the second PPG signal. If both the first PPG signal and the second PPG signal are above the signal quality metric threshold stored in memory element 122, the processor 120 can determine physiological information about the user based on the first PPG signal and the second PPG signal. If only one of the first PPG signal or the second PPG signal are above the signal quality metric threshold stored in memory element 122, the processor 120 can determine physiological information about the user based on the first PPG signal or the second PPG signal that are determined to be above the signal quality metric threshold.

In a number of embodiments, the processor 120 can average the first PPG signal and the second PPG signal with other electrical signals that exceed a stored PPG signal quality metric threshold. In some examples, the processor may be configured to identify PPG signals that were generated by optical receivers 110 that received optical signals that had a signal path 112 passing through a certain region of the wrist that may have fewer wrist structures 114. For instance, the processor 120 may be configured to identify one of the first PPG signal or the second PPG signal as associated with a signal path 112 passing through a portion of the user's wrist that is proximate to a certain region of the wrist or on the thumb side of a wrist of the user (as that portion of the wrist typically has fewer wrist structures 114 than the pinky finger side of the wrist) and apply a higher weighting to such PPG signals as such PPG signals may enable the processor 120 to determine accurate physiological information about the user, such as the user's heart rate and pulse oximetry.

In embodiments, the processor 120 may be able to determine that the wrist-worn electronic device 100 has been tightened beyond a transition point where the improvements in PPG signal quality from tightening wrist band 104 are negated by the adverse effects of the increased pressure associated with the increased compression. Once the processor 120 has determined that the wrist-worn electronic device 100 is likely being worn too tightly by the user 102, the processor 120 can determine and control a display to provide user recommendations to make appropriate adjustments to the band (e.g., wrist band 104 in FIGS. 1A-1B). For example, if the processor 120 determines that the current position or further tightening of the wrist band 104 is reducing the PPG signal quality, the processor 120 may control a display to present a recommendation for the user 102 to loosen the wrist band 104 and the extent to which the wrist band 104 should be loosened (e.g., one notch of the wrist band 104, two notches of the wrist band 104, etc.).

In embodiments, processor 120 can select one or more optical transmitter arrays 128 of the optical transmitter and receiver assembly 106 for use with determining physiological characteristics for the user, such as a heart rate, a heart rate variability, a blood pressure, peripheral oxygen saturation (e.g., SpO2), a stress intensity level, and a body energy level of the user based on a determined signal quality metric, such as signal-to-noise ratio, for the optical transmitter arrays 128. Processor 120 may select an optical transmitter array 128 for output of optical signals to produce PPG signals having an acceptable cardiac component within the PPG signal.

The one or more optical transmitter arrays 128 may be selected by the processor 120 based on an optimization of spectral properties of transmitted electromagnetic waves that would enable an optical receiver 110 to generate a PPG signal that may enable the processor 120 to determine accurate physiological information for the user. Generally, the optical receiver 110 generates a PPG signal by converting an intensity of the optical signal (e.g., a visible or invisible electromagnetic wave) reflected from the user's skin after it has passed through human tissue from an optical transmitter 108 of an optical transmitter array 128. Typically, the intensity of reflected light measured (e.g., sensed) by the optical receiver 110 is modulated by the subject's cardiac cycle, which causes variation in tissue blood volume during the cardiac cycle as the user's heart beats. The intensity of measured light is also strongly influenced by many factors other than the cardiac cycle. The other factors may include ambient light intensity including static and variable, body motion at the measurement location, static and variable sensor pressure on the user's skin, motion of the optical transmitter and receiver assembly 106 relative to the body at the measurement location, motion of the user breathing, and light barriers (e.g., hair, opaque skin layers, sweat, etc.). Relative to these sources, the cardiac component of the PPG signal may be very weak. In some instances, the cardiac component of the PPG signal may be lower than the other factors by one or more orders of magnitude, which can result in the cardiac component of the PPG signal having a low signal quality metric, such as signal-to-noise ratio.

The processor 120 can apply a filter to one or more PPG signals. For example, the processor 120 may apply a filter to isolate a common component, such as the cardiac (e.g., pulsatile) component, of a number of PPG signals and remove uncommon (undesired) components, such as noise. Because the cardiac component typically changes over time, such adaptive, time-varying filtering by the processor 120 may improve the quality of the cardiac component of PPG signals for subsequent analysis.

The memory element 122 can be a tangible, computer-readable storage medium that provides storage functionality to store various data and/or program code associated with an operation, such as software programs and/or code segments, or other data to instruct the processor 120, and possibly other components of the wrist-worn electronic device 100, to perform the functionality described herein. The memory element 122 can store data, such as program instructions for operating the wrist-worn electronic device 100 including its components, and so forth. The memory element 122 can also store signal quality metric thresholds, such as a signal-to-noise ratio threshold, heart rate information and/or oxygenation information determined for the user.

It should be noted that while a single memory element 122 is described, a wide variety of types and combinations of memory (e.g., tangible, non-transitory memory) can be employed. The memory element 122 can be integral with the processor 120, can comprise stand-alone memory, or can be a combination of both. Some examples of the memory element 122 can include removable and non-removable memory components, such as random-access memory (RAM), read-only memory (ROM), flash memory (e.g., a secure digital (SD) memory card, a mini-SD memory card, and/or a micro-SD memory card), magnetic memory, optical memory, universal serial bus (USB) memory devices, hard disk memory, external memory, and so forth. In a number of embodiments, the wrist-worn electronic device 100 and/or the memory element 122 can include removable integrated circuit card (ICC) memory, such as memory provided by a subscriber identity module (SIM) card, a universal subscriber identity module (USIM) card, a universal integrated circuit card (UICC), and so on.

The location determining element 130 generally determines a current geolocation of the wrist-worn electronic device 100 and may receive and process radio frequency (RF) signals from a multi-constellation global navigation satellite system (GNSS) such as the global positioning system (GPS) utilized in the United States, the Galileo system utilized in Europe, the GLONASS system utilized in Russia, or the like. The location determining element 130 may accompany or include an antenna to assist in receiving the satellite signals. The antenna may be a patch antenna, a linear antenna, or any other type of antenna that can be used with location or navigation devices. The location determining element 130 may include satellite navigation receivers, processors, controllers, other computing devices, or combinations thereof, and memory. The location determining element 130 may process a signal, referred to herein as a "location signal", from one or more satellites that includes data from which geographic information such as the current geolocation is derived. The current geolocation may include coordinates, such as the latitude and longitude, of the current location of the wrist-worn electronic device 100. The location determining element 130 may communicate the current geolocation to the processor 120, the memory element 122, or both.

Although embodiments of the location determining element 130 may include a satellite navigation receiver, it will be appreciated that other location-determining technology may be used. For example, cellular towers or any customized transmitting radio frequency towers can be used instead of satellites may be used to determine the location of the wrist-worn electronic device 100 by receiving data from at least three transmitting locations and then performing basic triangulation calculations to determine the relative position of the device with respect to the transmitting locations. With such a configuration, any standard geometric triangulation algorithm can be used to determine the location of the wrist-worn electronic device 100. The location determining element 130 may also include or be coupled with a pedometer, accelerometer, compass, or other dead-reckoning components which allow it to determine the location of the wrist-worn electronic device 100. The location determining element 130 may determine the current geographic location through a communications network, such as by using Assisted GPS (A-GPS), or from another electronic device, such as a fitness device or a mobile device (e.g., smartphone). The location determining element 130 may even receive location data directly from a user.

The display 132 generally presents the information mentioned above, such as time of day, current location, and the like. The display 132 may be implemented in one of the following technologies: light-emitting diode (LED), organic LED (OLED), Light Emitting Polymer (LEP) or Polymer LED (PLED), liquid crystal display (LCD), thin film transistor (TFT) LCD, LED side-lit or back-lit LCD, or the like, or combinations thereof. In some embodiments, the display 132 may have a round, circular, or oval shape. In other embodiments, the display 132 may possess a square or a rectangular aspect ratio which may be viewed in either a landscape or a portrait orientation.

The display 132 or user interface generally allows the user to directly interact with the wrist-worn electronic device 100 and may include pushbuttons, rotating knobs, or the like. In various embodiments, the display 132 may also include a touch screen occupying the entire display 132 or a portion thereof so that the display 132 functions as at least a portion of the user interface. The touch screen may allow the user to interact with the wrist-worn electronic device 100 by physically touching, swiping, or gesturing on areas of the display 132.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and methods are used. Therefore, the scope of one or more embodiments of the present disclosure should be determined with reference to the appended claims, along with the full range of equivalents to which such claims are entitled.

As used herein, "a number of" something can refer to one or more of such things. As will be appreciated, elements shown in the various embodiments herein can be added, exchanged, and/or eliminated so as to provide a number of additional embodiments of the present disclosure.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A wrist-worn electronic device, comprising:
    a housing including a bottom wall configured to contact a user's wrist;
    a first optical transmitter array positioned at a first location on the bottom wall and operable to output a plurality of first optical signals that pass through a user's skin, each first optical signal having a unique wavelength;
    a first optical receiver positioned at a second location on the bottom wall and operable to receive the first optical signals from the first optical transmitter array such that the first optical signals output by the first optical transmitter array travel along a first signal path from the first optical transmitter array to the first optical receiver and generate a first electronic signal corresponding to the first optical signals, the first signal path being substantially parallel to an arm axis of the user;
    a second optical transmitter array positioned at a third location on the bottom wall and operable to output a plurality of second optical signals that pass through the user's skin, each second optical signal having a unique wavelength;
    a second optical receiver positioned at a fourth location on the bottom wall and operable to receive the second optical signals from the second optical transmitter array such that the second optical signals output by the second optical transmitter array travel along a second signal path from the second optical transmitter array to the second optical receiver and generate a second electronic signal corresponding to the second optical signals, the second signal path being parallel to the arm axis of the user; and
    a processor coupled with the first optical receiver and the second optical receiver, the processor configured to:
    receive the first and the second electronic signals from the first and second optical receivers, respectively,
    determine a signal quality metric of each of the first electronic signal and the second electronic signal,
    determine physiological information about the user based on the first electronic signal if the determined signal quality metric of the first electronic signal is greater than the determined signal quality metric of the second electronic signal, and
    determine physiological information about the user based on the second electronic signal if the determined signal quality metric of the second electronic signal is greater than the determined signal quality metric of the first electronic signal.

2. The wrist-worn electronic device of claim 1, wherein the first location on the bottom wall of the first optical transmitter and the second location on the bottom wall of the first optical receiver are in an upper portion of the bottom wall; and
    wherein the third location on the bottom wall of the second optical transmitter and the fourth location on the bottom wall of the second optical receiver are in a lower portion of the bottom wall.

3. The wrist-worn electronic device of claim 2, wherein the first signal path from the first optical transmitter array to the first optical receiver passes through a first portion of the user's wrist, and wherein the second signal path from the second optical transmitter array to the second optical receiver passes through a second portion of the user's wrist.

4. The wrist-worn electronic device of claim 1, wherein the signal quality metric is a signal-to-noise ratio, and wherein the first and second optical transmitters are light-emitting diodes (LEDs) and the first and second optical receivers are photodiodes.

5. The wrist-worn electronic device of claim 1, wherein the arm axis of the user extends from the user's elbow to the user's hand of that arm.

6. The wrist-worn electronic device of claim 1, wherein the first signal path does not intersect the second signal path.

7. The wrist-worn electronic device of claim 1, further comprising a memory element configured to store a signal quality metric threshold.

8. The wrist-worn electronic device of claim 7, wherein the processor determines physiological information about the user based on the first electronic signal only if the signal quality metric of the first electronic signal is above the stored signal quality metric threshold, and wherein the processor determines physiological information about the user based on the second electronic signal only if the signal quality metric of the second electronic signal is above the stored signal quality metric threshold.

9. The wrist-worn electronic device of claim 1, wherein the plurality of first optical signals output by the first optical transmitter array and the plurality of second optical signals output by the second optical transmitter array, respectively, include a first wavelength between 600-680 nm, a second wavelength between 680-750 nm and a third wavelength between 750-950 nm.

10. A wrist-worn electronic device, comprising:
  a housing including a bottom wall configured to contact a user's wrist;
  a memory element configured to store a signal quality metric threshold;
  a first optical transmitter array positioned at a first location on the bottom wall and operable to output a plurality of first optical signals that pass through a user's skin, each first optical signal having a unique wavelength;
  a first optical receiver positioned at a second location on the bottom wall and operable to receive the first optical signals from the first optical transmitter array such that the first optical signals output by the first optical transmitter array travel along a first signal path from the first optical transmitter array to the first optical receiver and generate a first electronic signal corresponding to the first optical signals, the first signal path being substantially parallel to an arm axis of the user;
  a second optical transmitter array positioned at a third location on the bottom wall and operable to output a plurality of second optical signals that pass through the user's skin, each second optical signal having a unique wavelength;
  a second optical receiver positioned at a fourth location on the bottom wall and operable to receive the second optical signals from the second optical transmitter array such that the second optical signals output by the second optical transmitter array travel along a second signal path from the second optical transmitter array to the second optical receiver and generate a second electronic signal corresponding to the second optical signals, the second signal path being parallel to the arm axis of the user; and
  a processor coupled with the first optical receiver and the second optical receiver, the processor configured to:
  receive the first and the second electronic signals from the first and second optical receivers, respectively,
  determine a signal quality metric of each of the first electronic signal and the second electronic signal,
  compare the stored signal quality metric threshold with each of the determined signal quality metric of the first electronic signal and the second electronic signal,
  determine physiological information about the user based on the first electronic signal and the second electronic signal if the signal quality metric of the first electronic signal and the second electronic signal are above the stored signal quality metric threshold.

11. The wrist-worn electronic device of claim 10, wherein the first location on the bottom wall of the first optical transmitter and the second location on the bottom wall of the first optical receiver are in an upper portion of the bottom wall; and
  wherein the third location on the bottom wall of the second optical transmitter and the fourth location on the bottom wall of the second optical receiver are in a lower portion of the bottom wall.

12. The wrist-worn electronic device of claim 11, wherein the first signal path from the first optical transmitter array to the first optical receiver passes through a first portion of the user's wrist, and wherein the second signal path from the second optical transmitter array to the second optical receiver passes through a second portion of the user's wrist.

13. The wrist-worn electronic device of claim 10, wherein the signal quality metric is a signal-to-noise ratio, and wherein the first and second optical transmitters are light-emitting diodes (LEDs) and the first and second optical receivers are photodiodes.

14. The wrist-worn electronic device of claim 10, wherein the arm axis of the user extends from the user's elbow to the user's hand of that arm, and wherein the first signal path does not intersect the second signal path.

15. The wrist-worn electronic device of claim 10, wherein the plurality of first optical signals output by the first optical transmitter array and the plurality of second optical signals output by the second optical transmitter array, respectively, include a first wavelength between 600-680 nm, a second wavelength between 680-750 nm and a third wavelength between 750-950 nm.

16. A wrist-worn electronic device, comprising:
  a housing including a bottom wall configured to contact a user's wrist;
  a memory element configured to store a signal quality metric threshold;
  a first optical transmitter array positioned at a first location on the bottom wall and operable to output a plurality of first optical signals that pass through a user's skin, each first optical signal having a unique wavelength;
  a first optical receiver positioned at a second location on the bottom wall and operable to receive the first optical signals from the first optical transmitter array such that the first optical signals output by the first optical transmitter array travel along a first signal path from the first optical transmitter array to the first optical receiver and generate a first electronic signal corresponding to the first optical signals, the first signal path being substantially parallel to an arm axis of the user;
  a second optical transmitter array positioned at a third location on the bottom wall and operable to output a plurality of second optical signals that pass through the user's skin, each second optical signal having a unique wavelength;
  a second optical receiver positioned at a fourth location on the bottom wall and operable to receive the second optical signals from the second optical transmitter array such that the second optical signals output by the second optical transmitter array travel along a second signal path from the second optical transmitter array to the second optical receiver and generate a second electronic signal corresponding to the second optical signals, the second signal path being parallel to the arm axis of the user; and a processor coupled with the first optical receiver and the second optical receiver, the processor configured to:

receive the first and the second electronic signals from the first and second optical receivers, respectively, determine a signal quality metric of each of the first electronic signal and the second electronic signal, compare the stored signal quality metric threshold with each of the determined signal quality metric of the first electronic signal and the second electronic signal, and determine physiological information about the user based on the first electronic signal and the second electronic signal if the signal quality metric of the first electronic signal and the second electronic signal are above the stored signal quality metric threshold;

wherein the first location on the bottom wall of the first optical transmitter and the second location on the bottom wall of the first optical receiver are in an upper portion of the bottom wall; and wherein the third location on the bottom wall of the second optical transmitter and the fourth location on the bottom wall of the second optical receiver are in a lower portion of the bottom wall.

17. The wrist-worn electronic device of claim 16, wherein the first signal path from the first optical transmitter array to the first optical receiver passes through a first portion of the user's wrist, and wherein the second signal path from the second optical transmitter array to the second optical receiver passes through a second portion of the user's wrist.

18. The wrist-worn electronic device of claim 16, further comprising:

a third optical transmitter array positioned at a fifth location on the bottom wall and operable to output a plurality of third optical signals that pass through a user's skin, each third optical signal having a unique wavelength;

a third optical receiver positioned at a sixth location on the bottom wall and operable to receive the third optical signals from the third optical transmitter array such that the third optical signals output by the third optical transmitter array travel along a third signal path from the third optical transmitter array to the third optical receiver and generate a third electronic signal corresponding to the third optical signals, the third signal path being substantially parallel to an arm axis of the user;

wherein the processor is further configured to:

receive the third electronic signals from the third optical receiver, determine a signal quality metric of the third electronic signal, compare the stored signal quality metric threshold with the determined signal quality metric of the third electronic signal, and determine physiological information about the user based on the first electronic signal, the second electronic signal and the third electronic signal if the signal quality metric of the first electronic signal, the second electronic signal and the third electronic signal are above the stored signal quality metric threshold.

19. The wrist-worn electronic device of claim 16, wherein the signal quality metric is a signal-to-noise ratio, wherein the first and second optical transmitters are light-emitting diodes (LEDs) and the first and second optical receivers are photodiodes, wherein the arm axis of the user extends from the user's elbow to the user's hand of that arm, and wherein the first signal path does not intersect the second signal path.

20. The wrist-worn electronic device of claim 16, wherein the plurality of first optical signals output by the first optical transmitter array and the plurality of second optical signals output by the second optical transmitter array, respectively, include a first wavelength between 600-680 nm, a second wavelength between 680-750 nm and a third wavelength between 750-950 nm.

* * * * *